United States Patent [19]

Zink et al.

[11] Patent Number: 5,372,584
[45] Date of Patent: Dec. 13, 1994

[54] HYSTEROSALPINGOGRAPHY AND SELECTIVE SALPINGOGRAPHY

[75] Inventors: John N. Zink, Mountain View; Chris Decaria, Sunnyvale, both of Calif.; Jonathan Kagan, Minneapolis, Minn.; Robert S. Schenken, San Antonio, Tex.; Ricci Smelser, Monticello, Minn.

[73] Assignee: Ovamed Corporation, Sunnyvale, Calif.

[21] Appl. No.: 83,133

[22] Filed: Jun. 24, 1993

[51] Int. Cl.$^5$ ............... A61M 31/00; A61M 29/00; A61M 5/32
[52] U.S. Cl. .................. 604/55; 604/178; 604/96; 606/193
[58] Field of Search ............ 604/54, 55, 174, 176, 604/178, 96–103; 606/192, 193, 119; 128/778, 656–658; 600/35

[56] References Cited

U.S. PATENT DOCUMENTS

| | | |
|---|---|---|
| 3,421,509 | 1/1969 | Fiore . |
| 3,636,940 | 1/1972 | Gravlee . |
| 3,968,800 | 7/1976 | Vilasi . |
| 4,089,337 | 5/1978 | Kronner . |
| 4,160,446 | 7/1979 | Barrington .................. 604/55 X |
| 4,195,637 | 4/1980 | Gruntzig et al. . |
| 4,325,387 | 4/1982 | Helfer . |
| 4,430,076 | 2/1984 | Harris . |
| 4,502,482 | 3/1985 | DeLuccia et al. . |
| 4,655,214 | 4/1987 | Linder . |
| 4,997,419 | 3/1991 | Lakatos et al. ............... 604/55 |
| 5,104,377 | 4/1992 | Levine . |
| 5,108,366 | 4/1992 | Schatz . |
| 5,147,315 | 9/1992 | Weber ........................ 604/164 |
| 5,167,623 | 12/1992 | Cianci et al. . |
| 5,195,964 | 3/1993 | Kletzky et al. . |
| 5,205,831 | 4/1993 | Ryan et al. .................. 604/167 |
| 5,209,754 | 5/1993 | Ahluwalia .................... 606/119 |
| 5,217,466 | 6/1993 | Hasson ........................ 606/119 |
| 5,259,836 | 11/1993 | Thurmond et al. ........... 604/55 |

FOREIGN PATENT DOCUMENTS 2612783 9/1988 France ........................ 606/193

OTHER PUBLICATIONS

Publication, *Intrauterine Insemination*, Cook Urological Inc., Cover plus six pages, undated.
Sales Sheet, *Zinnanti Uterine Manipulator/Injector*, Zinnanti Surgical Instruments, Inc.; 4 pages; undated.

Primary Examiner—C. Fred Rosenbaum
Assistant Examiner—Adam J. Cermak
Attorney, Agent, or Firm—Nydegger & Associates

[57] ABSTRACT

An apparatus to establish access into the uterus and the fallopian tubes of a female for diagnostic or therapeutic procedures includes a cervical access catheter, an ostial access catheter insertable through the cervical access catheter, and a fallopian access catheter insertable through the ostial access catheter. The cervical access catheter incorporates a distally located intrauterine balloon which is inflatable after insertion into the uterus. The cervical access catheter also incorporates a cervical retention disk which can be slid into position against the anterior lip of the cervix to anchor the cervical access catheter into the cervical canal between the intrauterine balloon and the cervical disk. Once the cervical access catheter is properly anchored, the ostial access catheter is inserted through the cervical access catheter. The ostial access catheter has a guidable distal portion which, after the distal portion has passed through the cervical access catheter, can be positioned into the ostium of the fallopian tube. If desired, a contrast media can then be injected through the ostial access catheter. Further, if additional information is required, the fallopian access catheter can be inserted through the ostial access catheter and advanced into the fallopian tube for injection of a contrast media directly into the fallopian tube.

19 Claims, 4 Drawing Sheets

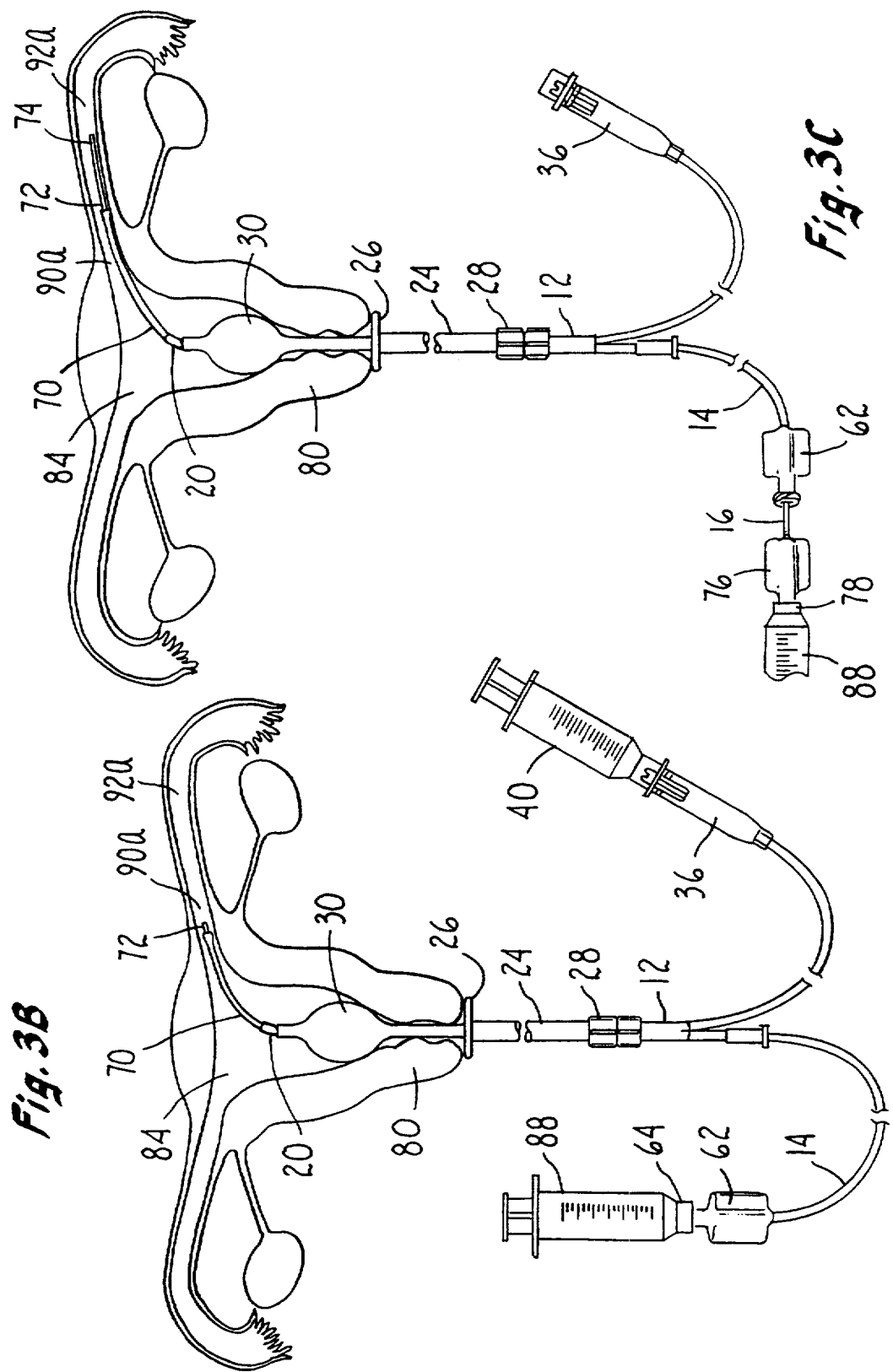

HYSTEROSALPINGOGRAPHY AND SELECTIVE SALPINGOGRAPHY

FIELD OF THE INVENTION

The present invention pertains generally to catheters and medical devices which are useful for diagnostic and therapeutic procedures involving the uterus and fallopian tubes of a female. More particularly, the present invention pertains to a system of catheters which interact to precisely establish an access path into the uterus and fallopian tubes for insertion of medical instruments or for the injection of a contrast media or other fluids. The present invention is particularly, but not exclusively, useful for hysterosalpingography and selective salpingography procedures.

BACKGROUND OF THE INVENTION

Hysterosalpingography is a well known medical procedure which involves recording images of anatomical structures of the uterus and fallopian uterine tubes. More specifically, during the procedure, an opaque or contrast media fluid is injected into the uterus and the fallopian tubes. Hysterosalpingography is used quite extensively to examine the uterus and fallopian tubes of a female for obstructions or anatomical abnormalities which might impair and prevent insemination or fertilization. It is a frequently performed procedure and to be effective it must, like other medically probative procedures, provide a high degree of accuracy in the resultant diagnosis.

There are, of course, other medical procedures wherein it is necessary to establish access or fluid communication with the uterus or the fallopian tubes. For instance, it is sometimes possible to inject fluid medicaments into the uterus or fallopian tubes for therapeutic purposes. Further, the insertion of instruments into the uterus or fallopian tubes may be indicated for procedures such as a biopsy. In any case, there are numerous procedures wherein it is desirable or necessary to establish access or fluid communication with either the uterus or the fallopian tubes.

Devices and systems which are presently being used to gain access for medical instruments into the uterus and fallopian tubes, or which are being used for the injection of a fluid contrast media into the uterus and fallopian tubes for a hysterosalpingography procedure, must pass through the cervix. Most incorporate a catheter which must somehow be anchored to the uterus to prevent dislodgment of the catheter during the procedure. How this is done, of course, differs from device to device. Several examples can be cited.

U.S. Pat. No. 5,104,377 which issued to Levine for an invention entitled "Uterine Access Device with Automatic Cervical Adjustment" discloses a device for accessing the uterus to either manipulate the uterus or to introduce fluids or other devices into it. To hold the device in place during its use, a distal balloon is inserted into the uterus and inflated while, at the same time, a proximal balloon is partially inserted into the cervical canal. The proximal balloon is then inflated, part of the inflated balloon is in the cervical canal and part is proximal to the exterior os of the cervix to capture the cervix between the inflated balloons, and thereby anchor the catheter. This can, however, be quite uncomfortable for the patient. Fluids can then be injected into the uterus through the catheter.

U.S. Pat. No. 4,089,337 which issued to Kronner for an invention entitled "Uterine Catheter and Manipulator with Inflatable Seal" discloses a flexible catheter which is inserted into the uterus against the resistive force of a spring biased disc. Once the catheter is positioned, a balloon is inflated in the uterus. The catheter is then anchored between opposing forces. One is the spring force of the spring biased disc, which tends to withdraw the catheter from the uterus. The other force is generated by the inflated balloon which resists the withdrawal. However, if the spring force is too weak, the catheter may be able to move back and forth through the cervical canal. This can cause trauma and can cause the distal tip of the catheter to move uncontrollably in the uterus. On the other hand, if the spring force is too strong, the cervix is pinched and there can be unwanted discomfort for the patient.

U.S. Pat. No. 4,430,076 which issued to Harris for an invention entitled "Combined Uterine Injector and Manipulative Device" discloses a multi-lumen catheter having a balloon which is inflatable once it is properly positioned in the uterus. A handle, which firmly engages the catheter, is prepositioned on the catheter to limit its insertion into the uterus. Depending upon the location where the handle is engaged with the catheter, the catheter is somewhat free to move back and forth through the cervical canal.

The examples of uterine catheters and injectors set forth above, all pertain to references which disclose devices that provide direct access only into the uterus. For hysterosalpingography this may be sufficient. On the other hand, it may not be sufficient. For instance, it is known that procedures which rely on the injection of a contrast media directly into the uterus, to obtain information about the condition of the fallopian tubes, result in approximately thirty to fifty (30–50%) false positive diagnoses for tubal obstruction. The unfortunate consequence of using systems and devices which provide direct access into only the uterus is; if it is ever determined that direct access into the fallopian tube is necessary, the system or device must be changed. Most often, this means there is a need for a second operation.

It can also happen that an incomplete or ineffective diagnosis may lead to unnecessary surgery. For example, the inability to determine the proper condition of the fallopian tubes may require an exploratory laparoscopy. Other examples can be given. Suffice it to say, any effective and efficacious intrauterine procedure is preferable.

In light of the above, it is an object of the present invention to provide a method and apparatus for establishing access or fluid communication with the uterus and the fallopian tubes of a female for diagnostic or therapeutic purposes which includes a cervical access catheter that can be adjusted according to the particular patient's anatomy to firmly, but gently, anchor the catheter across the cervical canal. It is another object of the present invention to provide a method and apparatus for establishing access or fluid communication with the uterus and the fallopian tubes which provides direct access into the fallopian tube. Still another object of the present invention is to provide a method and apparatus for establishing access or fluid communication with the uterus and the fallopian tubes which allows the flexibility of establishing direct access into the fallopian tube whenever it has been determined that access into only the uterus is ineffective for the particular diagnostic or therapeutic procedure. Another object of the present invention is to provide a method and apparatus for establishing access or fluid communication with the uterus and the fallopian tubes which is efficacious and, thereby, avoids unnecessary surgery. Yet another object of the present invention is to provide an apparatus for establishing access or fluid communication with the uterus and the fallopian tubes which is manufacturable, relatively easy to use, and comparatively cost effective.

SUMMARY OF THE INVENTION

In accordance with the present invention, an apparatus for establishing communication with the uterus and the fallopian tubes of a female includes the use of one, two, and possibly three, different catheters. First, there is a dual lumen cervical access catheter (hereinafter sometimes referred to as "CAC") which is anchorable across the cervical canal to establish extracorporeal access into the uterus. Second, there is a single lumen ostial access catheter (hereinafter sometimes referred to as "OAC") which is insertable through the CAC. The distal portion of the OAC is preformed and bent to be deflectable or steerable to allow its distal end to be guided into position against the ostium of the fallopian tube. Finally, there is a single or dual lumen fallopian access catheter (hereinafter sometimes referred to as "FAC") which is insertable through the OAC for advancement into the fallopian tube.

If the CAC proves to be sufficient and effective for the particular procedure, only the CAC need be used to establish fluid communication with the uterus. However, if the CAC, alone, is insufficient or ineffective, the OAC may be inserted through the CAC and its distal end guided into position through the ostium of the fallopian tube. Further, if the CAC proves to be insufficient or ineffective, the FAC can be inserted through the OAC to establish fluid communication directly into the fallopian tube. For each step, there is no need to remove or replace any part of the system already employed.

As intended for the present invention, the cervical access catheter (CAC) is an elongated catheter which, as indicated above, has two lumens. One lumen is a working channel that extends through the length of the CAC. The other lumen of the CAC is an inflation lumen.

An inflatable intrauterine balloon is located distally on the CAC and is joined in fluid communication with the inflation lumen at its distal end. At the proximal end of the inflation lumen, i.e. the end opposite the intrauterine balloon, a pilot balloon and check valve assembly are also joined in fluid communication with the inflation lumen. During operation of the present invention, the intrauterine balloon is inserted into the uterus while the pilot balloon and check valve assembly remain extracorporeal.

The CAC also includes a fixation member which is slidably disposed around the body of the CAC. The fixation member has a cervical retention disk which can be positioned against the anterior lip of the cervix. It also has a locking mechanism which can be manipulated to selectively secure the fixation member onto the body of the CAC.

Both the CAC and the OAC can include fluid seals which are located proximally in the lumen of the respective catheter, and which are engageable with any device or other catheter that may be inserted into the lumen. As intended for the present invention, these seals are provided to establish a fluid seal between the catheter and the inserted device whenever the apparatus is being used to inject a fluid into the uterus or the fallopian tubes. Further, in addition to providing for fluid access into the uterus and fallopian tubes of a female, the catheter of the present invention also establishes an access route into these anatomical structures for other devices.

In the operation of the present invention, the intrauterine balloon of the cervical access catheter (CAC) is first deflated and inserted into the uterus. An inflation syringe is then connected to the inflation lumen, through the check valve, and the intrauterine balloon is inflated to prevent withdrawal of the CAC from the uterus. At this time the pilot balloon, which remains extracorporeal, will also be inflated to give the user a visual indication that the intrauterine balloon has been inflated.

With the intrauterine balloon inflated in the uterus, the fixation member is slid along the body of the CAC to position the cervical retention disk against the anterior lip of the cervix. The locking mechanism of the fixation member is then manipulated to secure the fixation member onto the CAC. This anchors the CAC across the cervical canal between the counteractive forces of the intrauterine balloon and the cervical retention disk. The CAC thus establishes fluid communication with the uterus, and a fluid can be injected through the CAC directly into the uterus.

As needed, the ostial access catheter (OAC) is inserted through the working channel of the CAC and then guided to position the distal tip of the OAC against the ostium of the fallopian tube. With the distal tip of the OAC so positioned, a contrast media or some other media can be injected through the lumen of the OAC and into the fallopian tube for therapeutic or diagnostic purposes. Depending upon the results obtained using the OAC, and the desires of the operator, more positive injection of a media into the fallopian tube can be realized using the fallopian access catheter (FAC). To do so, the FAC is inserted through the lumen of the OAC and advanced through the ostium of the fallopian tube and into the fallopian tube itself. A fluid media can then be injected through the lumen of the FAC and into the fallopian tube for surgical or diagnostic purposes.

BRIEF DESCRIPTION OF THE DRAWINGS

The novel features of this invention, as well as the invention itself, both as to its structure and its operation will be best understood from the accompanying drawings, taken in conjunction with the accompanying description, in which similar reference characters refer to similar parts, and in which:

FIG. 3B is a representational view of the cervical access catheter anchored into the cervical canal of a female, with the distal portion of the ostial access catheter being inserted through the cervical access catheter and into position against the ostium of a fallopian tube for injection of a contrast media;

FIG. 3C is a representational view of the cervical access catheter and ostial access catheter as shown in FIG. 3A with a fallopian access catheter inserted through the ostial access catheter and advanced into the fallopian tube for injection of a contrast media;

DESCRIPTION OF THE PREFERRED EMBODIMENTS

Figure 1:
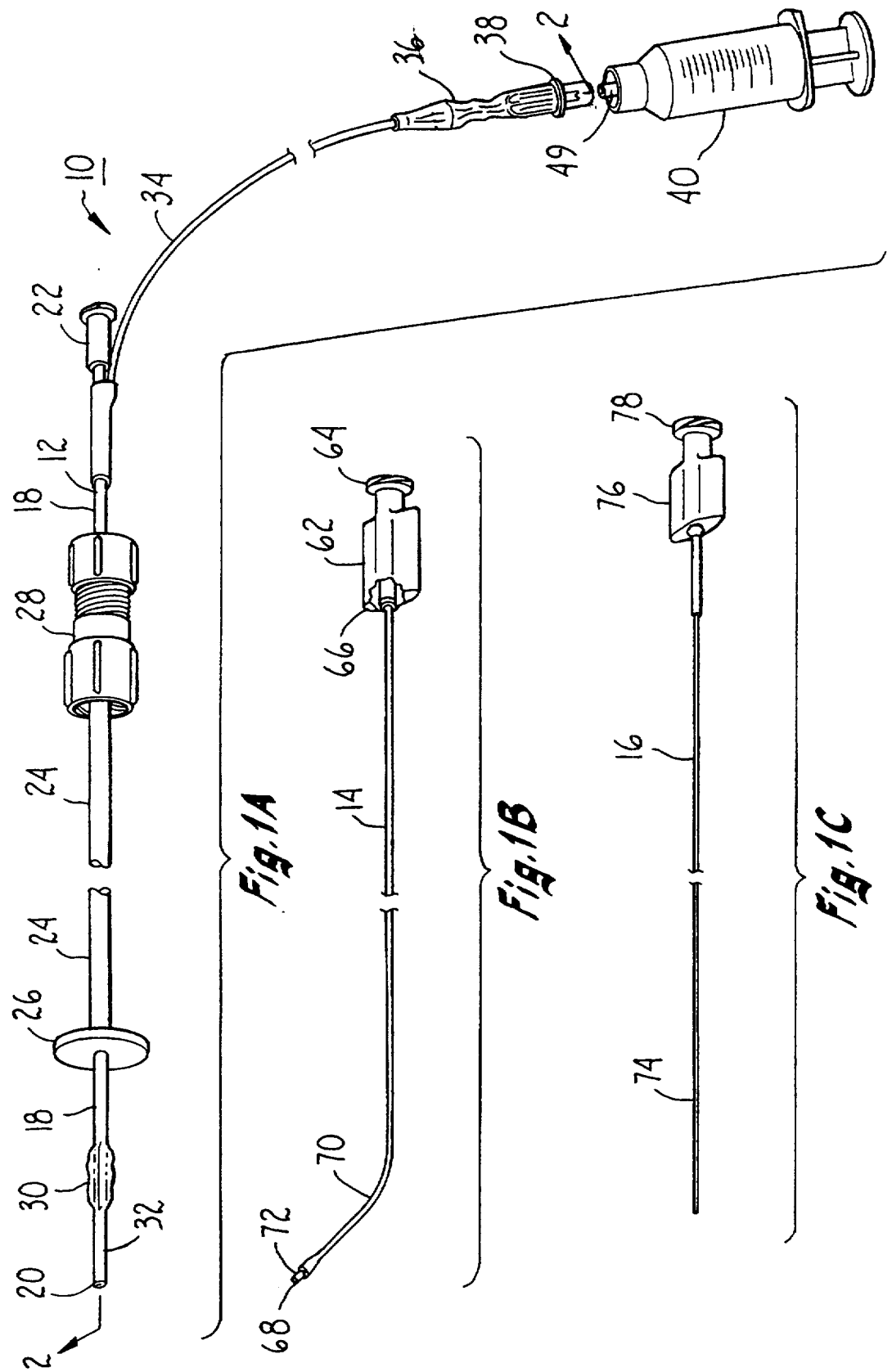
FIG. 1A is a perspective view of the cervical access catheter of the present invention.
FIG. 1B is a perspective view of the ostial access catheter of the present invention with portions cut away for clarity.
FIG. 1C is a perspective view of the fallopian access catheter of the present invention.

Referring to the drawings, an apparatus for establishing fluid communication with the uterus and the fallopian tubes of a female is shown collectively in FIGS. 1A, 1B and 1C and is generally designated 10. As shown, the apparatus 10 includes three separate catheters. These include: a cervical access catheter (CAC) 12 shown in FIG. 1A; an ostial access catheter (OAC) 14 shown in FIG. 1B; and a fallopian access catheter (FAC) 16 shown in FIG. 1C. As intended for the operation of apparatus 10, in a manner to be subsequently disclosed, OAC 14 is insertable through CAC 12, and FAC 16 is insertable through OAC 14.

FIG. 1A indicates that the CAC 12 has an elongated tubular body 18 which extends from a distal tip 20 to a proximally located connector 22. Slidably mounted on the body 18 of CAC 12 is a fixation member 24 which includes a semi-rigid cervical retention disk 26 and a locking mechanism 28. As shown, the cervical retension disk 26 is located distally on the fixation member 24 while a locking mechanism 28 is located proximally on the fixation member 24.

Still referring to FIG. 1A, it can be seen that an inflatable intrauterine balloon 30 is located on the distal portion 32 of body 18. In FIG. 1A the intrauterine balloon 30 is shown deflated. Further, it will also be seen that a fluid line 34 is connected to the proximal portion of body 18 of CAC 12, and that a pilot balloon 36 and a check valve 38 are located proximally on the line 34. Like balloon 30, the pilot balloon 36 is shown deflated in FIG. 1A. An inflation syringe 40 is shown poised in FIG. 1A for engagement with the check valve 38.

Figure 2:
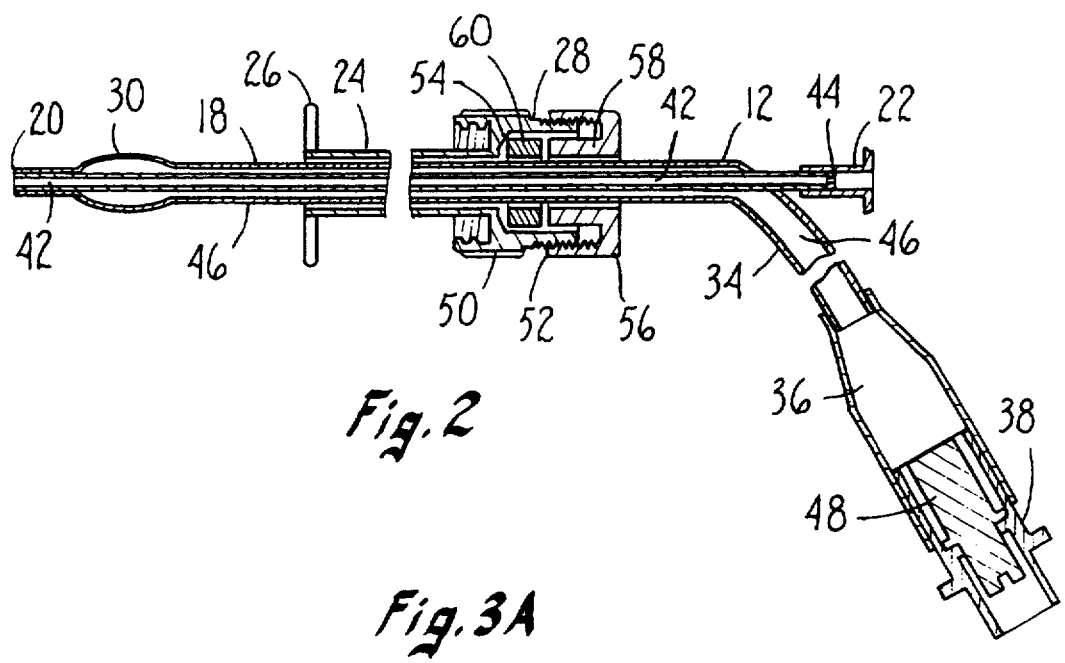
FIG. 2 is a cross-sectional view of the cervical access catheter of the present invention as seen along the line 2—2 in FIG. 1A.

In FIG. 2, a more detailed drawing of the inside components of CAC 12 is presented. There it will be seen that the body 18 of CAC 12 is formed with a working channel 42 which extends the length of the body 18. Also, at the proximal end of the working channel 42, there is a fluid seal 44. As intended for apparatus 10, in addition to providing a possible fluid communication path, the working channel 42 of CAC 12 is dimensioned to selectively receive OAC 14. Thus, whenever OAC 14 is inserted into the working channel 42 of CAC 12, fluid seal 44 will contact OAC 14 to establish a fluid seal between CAC 12 and OAC 14.

In accordance with the present invention, the fluid seal 44 and any other fluid seals which might be incorporated for use in apparatus 10 can be of several types. Specifically, fluid seal 44 may be a self adjustable seal, sometimes also known as a gland seal, which is typically a membrane with a hole or slit through which a catheter or some other device can be inserted. Also, fluid seal 44 may be a non-adjustable seal, such as an O-ring or a Quad-ring. Further, fluid seal 44 can be a manually adjustable seal. In all cases, the fluid seal 44 can either be permanently affixed to the CAC 12, or it can be removable or separable. Preferably, for the present invention, fluid seal 44 is a non-adjustable seal such as a Quad-ring.

FIG. 2 also shows that line 34 forms part of an inflation lumen 46 which extends continuously between the intrauterine balloon 30 and the pilot balloon 36. Additionally, check valve 38 is shown to include a piston 48 which is moveable to gain fluid access to inflation lumen 46. With this structure, whenever inflation syringe 40 is engaged with check valve 38, piston 48 is depressed by the tip 49 of syringe 40 to establish fluid communication with inflation lumen 46 through check valve 38. The inflation syringe 40 can then be operated to simultaneously inflate both the intrauterine balloon 30 and the pilot balloon 36. Upon disengagement of inflation syringe 40 from check valve 38, piston 48 will move back to its position shown in FIG. 2 to prevent the escape of fluid from the balloons 30 and 36 and leave them in an inflated configuration. Deflation of the balloons 30 and 36 can be accomplished merely by reengaging syringe 40 with check valve 38 and appropriately manipulating inflation syringe 40.

As also shown in FIG. 2, the locking mechanism 28 of CAC 12 includes a base 50 which is fixedly connected to the cervical retention disk. Further, the base 50 is formed with a cavity 52 that has a tapered shoulder 54. An engager 56 having a protrusion 58 is rotatably and threadably joined to the base 50 to position the protrusion 58 in the cavity 52 substantially as shown. A gripping ring 60, made of a resilient material, is located in the cavity 52 between protrusion 58 of engager 56 and the tapered shoulder 54 of base 50. Consequently, when engager 56 is rotated to advance protrusion 58 into cavity 52, the protrusion 58 urges gripping ring 60 against the shoulder 54. This, in turn, causes gripping ring 60 to deform and urge against the body 18 of CAC 12. This action of the ring 60 against body 18 secures fixation member 24 from further sliding movement along the body 18 of CAC 12. On the other hand, a counter rotation of the engager 56 withdraws protrusion 58 from the cavity 52 to release the effect of gripping ring 60 for subsequent movement of fixation member 24 along body 18 of CAC 12.

Returning now to FIG. 1B, it will be seen that the ostial access catheter (OAC) 14 incorporates a handle 62 and has a luer connector 64 at its proximal end. For purposes of the present invention, OAC 14 is made of any well known suitable material which exhibits good torque control through the length of OAC 14, such as nylon, polyethylene, or a composite. In the cut away portion of FIG. 1B it can be seen that OAC 14 includes an fluid seal 66, such as a Quad-ring, which is located around the periphery of lumen 68. Thus, whenever FAC 16 is inserted through lumen 68 of OAC 14, fluid seal 66 will create a fluid seal between OAC 14 and FAC 16.

Additionally, as indicated in FIG. 1B, the distal portion 70 of OAC 14 is bendable into a configuration, substantially as shown. Preferably, distal portion 70 is prebent so that rotation of the handle 62 will result in a rotation of the distal portion 70 about the axis of OAC 14. In alternate embodiments, however, it is appreciated that the distal portion 70 may initially be straight and then selectively bent with manipulation controls (not shown) to configure OAC 14 as desired. It is also indicated in FIG. 1B that OAC 14 may include a soft tip 72. For purposes of the present invention, soft tip 72 is made of any compatible material well known in the art which will serve as a slight extension of the lumen 68 and which will deform slightly on contact with body tissue to reduce and minimize trauma to tissue in the uterus and fallopian tubes.

FIG. 1C shows that the FAC 16 of apparatus 10 includes an elongated tubular body 74. The body 74 is flexible, so it can be inserted through lumen 68 of OAC 14, and it is formed with a lumen that extends throughout its length. FAC 16 also includes a handle 76 which is located proximally on tubular body 74, and a luer connector 78 which is located at the proximal end of FAC 16.

Figure 4A:
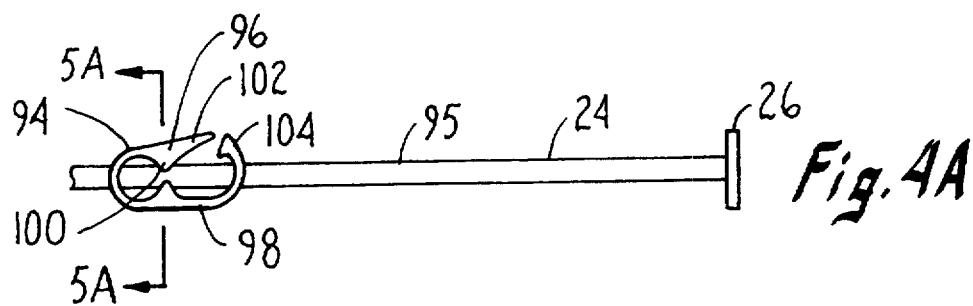
FIG. 4A is a side elevational view of an alternate embodiment of the fixation member of the present invention with its clamp open.
Figure 4B:
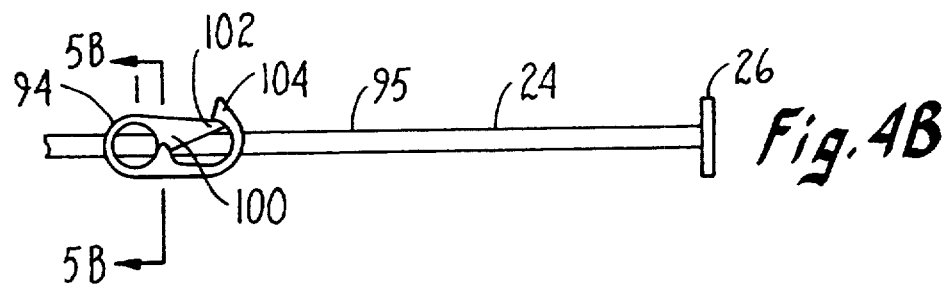
FIG. 4B is a side elevational view of the fixation member shown in FIG. 4A with its clamp closed.

Turning for the moment to FIG. 4A, an alternate embodiment is shown for fixation member 24. Specifically, this embodiment includes a clamp 94 which is fixedly attached to the body 95 of fixation member 24. As shown, clamp 94 includes and upper arm 96 and a lower arm 98. Further, the clamp 94 has a grip 100 which is formed into the upper arm 96. The clamp 94 is made of a semi rigid, but flexible, material so that the upper arm is pivotable relative to the lower arm 98. Consequently, the protrusion 102 of upper arm 96 is engageable with the hook 104 of lower arm 98 to hold clamp 94 in a configuration as shown in FIG. 4B. As intended for the present invention, protrusion 102 and hook 104 can be manipulated for engagement (FIG. 4B) or disengagement (FIG. 4A).

Figure 5A:
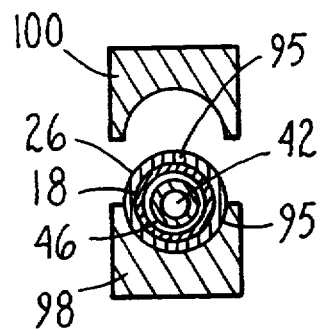
FIG. 5A is a cross sectional view of the clamp of the alternate embodiment of the fixation member of the present invention as seen along the line 5A—5A in FIG. 4A.
Figure 5B:
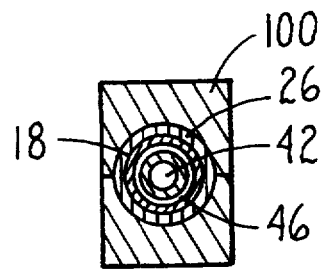
FIG. 5B is a cross sectional view of the clamp of the alternate embodiment of the fixation member of the present invention as seen along the line 5B—5B in FIG. 4B.

As indicated in FIG. 5A, the body 95 of clamp 94 may be fixedly attached to the lower arm 98 of clamp 94. Then, when upper arm 96 is moved to engage protrusion 102 with hook 104, grip 100 will lower onto body 95 to confine body 95 between the grip 100 and lower arm 98 in a manner as shown in FIG. 5B. Additionally, with this action, the body 95 will be deformed slightly to establish a frictional or interference engagement between the body 95 of fixation member 24 and the body 18 of CAC 12. As will be appreciated by those skilled in the art, this captures fixation member 24 on CAC 12 to hold the cervical disk 26 in a desired location relative to the intrauterine balloon 30. Thus, with proper manipulation of clamp 94, CAC 12 can be anchored across the cervical canal of a female as desired.

Figure 6:
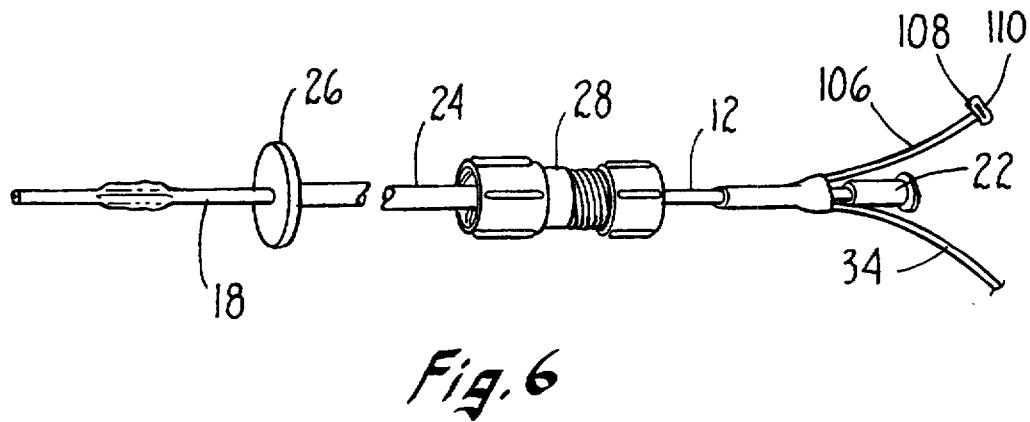
FIG. 6 is a perspective view of an alternate embodiment of the cervical access catheter of the present invention.

FIG. 6 shows an alternate embodiment for the CAC 12 of the present invention wherein CAC 12 includes an additional fluid access line 106. As intended for the present invention, the fluid access line 106 is in fluid communication with working channel 42 of CAC 12. This is provided to establish fluid communication with working channel 42 whenever OAC 14, or some other device has been inserted through proximal connector 22 and into working channel 42. As shown in FIG. 6, fluid access line 106 includes a connector 108 and a removable cap 110. Thus, when fluid line 106 is to be used, the cap 110 can be removed and a fluid device (not shown) may be attached to the connector 108 for injection of fluid into the working channel 42.

OPERATION

Figure 3A:
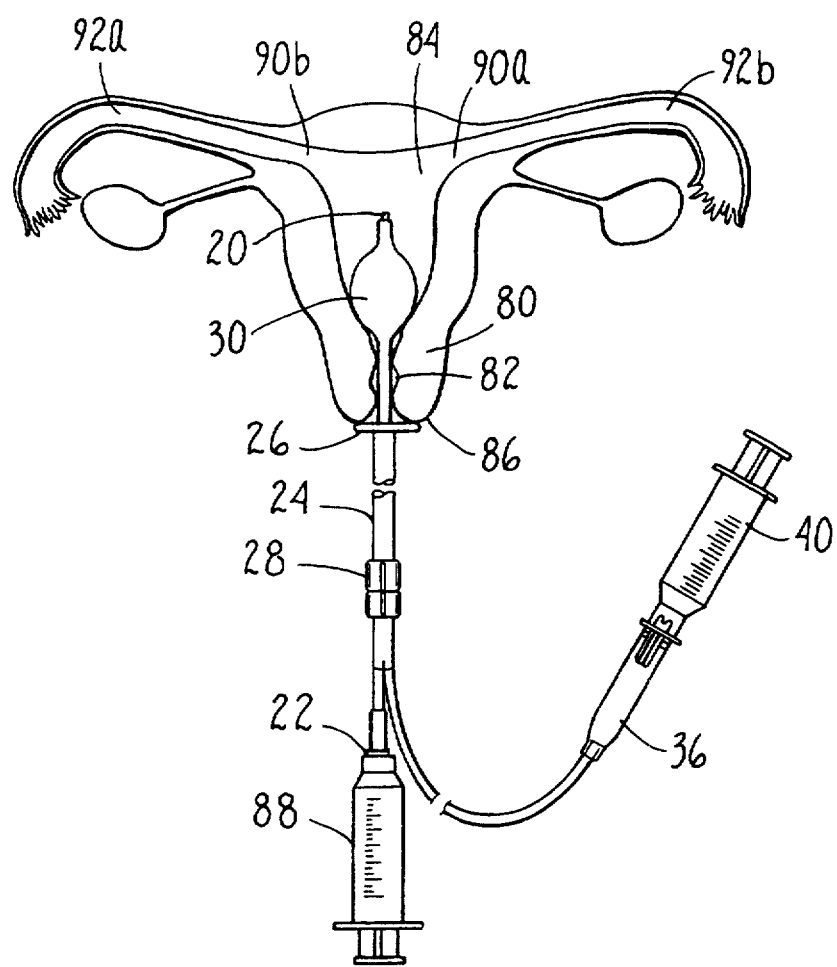
FIG. 3A is a representational view of the cervical access catheter of the present invention anchored into the cervical canal of a female.

In the operation of the apparatus 10 of the present invention, the user first works with CAC 12. To begin, inflation syringe 40 is engaged with check valve 38 and the syringe 40 is manipulated to deflate both the intrauterine balloon 30 and the pilot balloon 36. As indicated in FIG. 3A, distal tip 20 of CAC 12 is inserted through the cervix 80, more specifically through cervical canal 82, and into the uterus 84. The insertion of distal tip 20 is sufficient to also position the deflated intrauterine balloon 30 in uterus 84. With balloon 30 so positioned, inflation syringe 40 is again engaged with check valve 38 and manipulated to inflate both intrauterine balloon 38 and pilot balloon 36. As stated above, visual observation of pilot balloon 36 gives an indication of the inflated state of the intrauterine balloon 30.

With intrauterine balloon 30 inflated in the uterus 84, fixation member 24 is slidingly advanced along body 18 of CAC 12 until cervical retention disk 26 comes into contact with the anterior lip 86 of cervix 80. As will be appreciated by the skilled artisan, retention disk 26 can be gently placed against anterior lip 86 while the inflated balloon 30 is held against the posterior portion of cervical canal 82. Locking mechanism 28, which remains extracorporeal, is then manipulated to tighten fixation member 24 onto body 18 of CAC 12. With this step, the cervical retention disk 26 is firmly held on CAC 12 and in a stationary relationship thereto.

Once fixation member 24 is tightened onto CAC 12, the CAC 12 is anchored to the cervix 80. Specifically, this anchoring of CAC 12 to cervix 80 is accomplished by the opposing actions of the inflated intrauterine balloon 30 and the cervical retention disk 26. More specifically, balloon 30 acts against the posterior portion of cervical canal 82 to prevent withdrawal of the CAC 12 from the uterus 84, and cervical retention disk 26 acts against anterior lip 86 to prevent further insertion of CAC 12 into the uterus 84.

With the distal tip 20 of CAC 12 positioned in uterus 84, the user can selectively engage a fluid source 88, such as the syringe shown in FIG. 3A, to the connector 22 of CAC 12 for the injection of fluids into uterus 84. As intended for the present invention, the particular fluid to be injected into uterus 84 is discretionary according to the desires and needs of the user. For example, the fluid can be a contrast media of any type well known in the pertinent art which is useful for hysterosalpingography or selected salpingography procedures. Further, the fluid can be a medicament which will have a therapeutic effect on the tissues with which it comes into contact.

For the particular circumstance shown in FIG. 3A, the fluid is to be injected directly into the uterus 84. From there, under normal conditions, the fluid can travel through either ostium 90a or 90b and into the respective fallopian tube 92a or 92b. It can happen for several different reasons, however, that either one or both of the fallopian tubes 92 a,b will not be filled with injected fluid when fluid is injected fluid directly into only the uterus 84. Thus, if the particular anatomical area of interest is in the fallopian tube 92, it may be necessary to use OAC 14.

FIG. 3B shows that OAC 14 has been inserted through the working channel 42 of the anchored CAC 12 and advanced to the point where its distal portion 70 is located in uterus 84. Once distal portion 70 is in uterus 84 it is possible to move distal portion 70 and position it into the ostium 90 of a selected fallopian tube 92. In FIG. 3B, distal portion 70 is specifically shown positioned in ostium 90a of fallopian tube 92a. As indicated above, distal portion 70 may be prebent to help accomplish this function. If so, the handle 62 of OAC 14 can be rotated, with a consequent rotation of distal portion 70, until the soft tip 72 is positioned in ostium 90 as desired. Alternatively, as also indicated above, distal portion 70 can be bendable or deflectable by incorporating a mechanism (not shown) of a type well known in the art, which can be used to bend guidewires and catheters. In either case, for the present invention, it is intended that the distal portion 70 of OAC 14 be guidable to position the distal tip 72 into the ostium 90 of a fallopian tube 92.

As indicated in FIG. 3B, once OAC 14 has been positioned, fluid source 88 can be engaged with the luer connector 64. This places fluid source 88 in fluid communication with the lumen 68 of OAC 14 and allows fluid to be injected directly into the fallopian tube 92 through the ostium 90. As before, the particular fluid to be injected is discretionary to the user and will depend upon the particular procedure to be performed. Unfortunately, it may happen that even this is ineffective for injecting fluid into the particular part of fallopian tube 92 which is of interest. If so, it will be necessary to use FAC 16.

FIG. 3C indicates that the FAC 16 can be used in conjunction with the prepositioned CAC 12 and OAC 14. Specifically, the body 74 of FAC 16 is inserted through lumen 68 of OAC 14 and advanced until its distal tip is extended past the distal tip 72 of OAC 14. As indicated in FIG. 3C, this action will position the distal end of FAC 16 well inside the fallopian tube 92. With FAC 16 positioned as desired, the operator is then able to engage the fluid source 88 with luer connector 78 to establish fluid communication between fluid source 88 and the lumen of FAC 16. Again, the fluid to be injected is discretionary according to the needs and desires of the operator.

To disengage the apparatus 10, the inflation syringe 40 is engaged with the check valve 38 of CAC 12 and manipulated to deflate the intrauterine balloon 30. The entire apparatus 10, including CAC 12 alone or in combination with OAC 14 or FAC 16, can then be withdrawn from the patient.

While the particular apparatus for establishing fluid communication with the uterus and fallopian tubes as herein shown and disclosed in detail is fully capable of obtaining the objects and providing the advantages herein before stated, it is to be understood that it is merely illustrative of the presently preferred embodiments of the invention and that no limitations are intended to the details of the construction or design herein shown other than as defined in the appended claims.

We claim:

1. An apparatus for establishing access to the uterus and fallopian tube of a female which comprises:
    cervical access means for establishing a working channel through the cervix into the uterus, said cervical access means being anchorable in the cervical canal for establishing fluid tight extracorporeal access into the uterus through said working channel;
    ostial access means for establishing access into the ostium of a fallopian tube, said ostial access means being selectively insertable through said working channel of said cervical access means, said ostial access means formed with a lumen and having a distal end with a distal end portion adjacent said distal end, and having a proximal end with a proximal end portion adjacent said proximal end, said ostial access means being guidable to position said distal end thereof into the ostium of the fallopian tube;
    fallopian access means for establishing access into the fallopian tube, said fallopian access means being selectively insertable through said lumen of said ostial access means for advancement of said fallopian access means into the fallopian tube; and
    an O-ring mounted in said proximal portion of said ostial access means to establish a fluid seal between said ostial access means and said fallopian access means.

2. An apparatus as recited in claim 1 wherein said cervical access means is an elongated cervical access catheter having a distal end with a distal end portion adjacent thereto and having a proximal end with a proximal end portion adjacent thereto, and wherein said working channel extends through said cervical access catheter and wherein said cervical access catheter further comprises:
    an inflatable intrauterine balloon located on said distal end portion of said cervical access catheter for passage through the cervical canal and inflation in the uterus;
    a cervical retention disk slidably mounted on said cervical access catheter;
    a fixation member attached to said cervical retention disk, said fixation member being slidably mounted on said cervical access catheter to position said disk against the anterior lip of the cervix while said inflatable balloon is in the uterus; and
    a locking mechanism mounted on said fixation member to selectively grip said cervical access catheter for holding said fixation member in place on said cervical access catheter.

3. An apparatus as recited in claim 2 wherein said cervical access catheter further comprises:
    an inflation lumen having a distal end and a proximal end, said distal end of said inflation lumen being connected with said inflatable intrauterine balloon for fluid communication therebetween;
    a pilot balloon assembly connected in fluid communication with said proximal end of said inflation lumen;
    a check valve connected in fluid communication with said pilot balloon assembly; and
    an inflation syringe engageable with said check valve for simultaneously inflating said intrauterine balloon and said pilot balloon.

4. An apparatus as recited in claim 2 wherein said cervical access catheter includes a fluid seal mounted in said working channel in said proximal portion of said cervical access catheter to establish a fluid barrier between said cervical access catheter and said ostial access means and wherein said ostial access means is an ostial access catheter insertable through said working channel of said cervical access catheter to extend said distal end portion of said ostial access catheter beyond said distal end of said cervical access catheter, said distal end portion of said ostial access catheter being guidable for placement of said distal end of said ostial access catheter against the ostium of the fallopian tube.

5. An apparatus for establishing fluid communication with the uterus and fallopian tube of a female which comprises:

- an elongated cervical access catheter for accessing the cervix, said cervical access catheter being anchorable in the cervical canal for establishing extracorporeal access into the uterus, said cervical access catheter being formed with a working channel having a distal end with a distal portion adjacent thereto and having a proximal end with a proximal end portion adjacent thereto, said working channel extending through said cervical access catheter;
- a first sealing means for establishing a fluid tight seal for said cervical access catheter, said first sealing means being mounted in said proximal portion of said working channel of said cervical access catheter;
- an inflatable intrauterine balloon located on said distal end portion of said cervical access catheter for passage through the cervical canal and inflation in the uterus;
- a cervical disk slidably mounted on said cervical access catheter;
- a fixation member formed with said cervical disk, said fixation member being slidably mounted on said cervical access catheter to position said disk against the anterior lip of the cervix while said inflatable balloon is in the uterus;
- a locking mechanism mounted on said fixation member to selectively grip said cervical access catheter for holding said fixation member in place on said cervical access catheter;
- a first fluid source selectively engageable in fluid communication with said working channel;
- an ostial access catheter for establishing access to the ostium of a fallopian tube, formed with a lumen, said ostial access catheter having a distal end and a distal end portion adjacent said distal end thereof and a proximal end and a proximal end portion adjacent said proximal end thereof, said ostial access catheter being insertable through said first sealing means into said working channel of said cervical access catheter to extend said distal end portion of said ostial access catheter beyond said distal portion of said cervical access catheter, said distal end portion of said ostial access catheter being preformed for guidable placement of said distal end of said ostial access catheter against the ostium of the fallopian tube;
- a second sealing means for establishing a fluid tight seal for said ostial access catheter, said second sealing means being mounted in said proximal portion of said lumen; and
- a second fluid source selectively engageable in fluid communication with said lumen of said ostial access catheter.

6. An apparatus as recited in claim 5 further comprising:

- a fallopian access catheter for establishing access to the fallopian tubes, formed with a lumen, having a distal end and a proximal end, said fallopian access catheter being insertable through said second sealing means into said lumen of said ostial access catheter to extend said distal end of said fallopian access catheter beyond said distal end of said ostial access catheter, through the ostium of the fallopian tube and into the fallopian tube; and
- a third fluid source selectively engageable in fluid communication with said lumen of said fallopian access catheter.

7. An apparatus as recited in claim 6 wherein said cervical access catheter further comprises:

- an inflation lumen having a distal end and a proximal end, said distal end of said inflation lumen being connected with said inflatable intrauterine balloon for fluid communication therebetween;
- a pilot balloon assembly connected in fluid communication with said proximal end of said inflation lumen;
- a check valve connected in fluid communication with said pilot balloon assembly; and
- an inflation syringe engageable with said check valve for simultaneously inflating said intrauterine balloon and said pilot balloon.

8. An apparatus as recited in claim 7 wherein said first sealing means is a Quad-ring mounted in said working channel in said proximal portion of said cervical access catheter to establish a fluid seal between said cervical access catheter and said ostial access catheter, and said second sealing means is an O-ring mounted in said lumen in said proximal portion of said ostial access catheter to establish a fluid seal between said ostial access catheter and said fallopian access catheter.

9. A method for establishing fluid communication with the uterus and fallopian tubes of a female using an apparatus including a fluid source, an elongated cervical access catheter for establishing access to the cervix, formed with a working channel, an inflatable intrauterine balloon located distally on said cervical access catheter, a check valve connected in fluid communication with said balloon, a fixation member formed with a cervical retention disk and having a manipulable locking mechanism, said fixation member being slidably mounted on said cervical access catheter; an ostial access catheter for establishing access to the ostium of a fallopian tube, formed with a first lumen, said ostial access catheter being insertable through said working channel of said cervical access catheter and said ostial access catheter having a guidable distal end portion for placement of said distal end portion; a fallopian access catheter for establishing access to the fallopian tubes, formed with a second lumen, said fallopian access catheter being insertable through said lumen of said ostial access catheter; a fluid tight seal in said cervical access catheter working channel to establish a fluid barrier between said cervical access catheter and said ostial access catheter; and a fluid tight seal in said lumen of said ostial access catheter to establish a fluid barrier between said ostial access catheter and said fallopian access catheter; said method comprising the steps of:

- inserting said intrauterine balloon through the cervical canal and into the uterus;
- inflating said intrauterine balloon;
- positioning said retention disk of said fixation member against the anterior lip of the cervix;
- anchoring said cervical access catheter in the cervical canal by manipulating said locking mechanism of said fixation member; and
- selectively engaging said fluid source in fluid communication with one of said working channel, said first lumen, or said second lumen, to inject fluid into the uterus or the fallopian tube.

10. A method as recited in claim 9 further comprising the steps of:

inserting said ostial access catheter through said working channel of said cervical access catheter;

Positioning said distal portion of said ostial access catheter against the ostium of a fallopian tube; and selectively engaging said fluid source in fluid communication with said lumen of said ostial access catheter for injection of fluid into the fallopian tube.

11. A method as recited in claim 10 further comprising the steps of:

inserting said fallopian access catheter through said lumen of said ostial access catheter for advancing a portion of said fallopian access catheter into the fallopian tube; and connecting said source of contrast media with said lumen of said fallopian access catheter for selective injection of fluid into the fallopian tube.

12. A method as recited in claim 9 wherein said apparatus includes a pilot balloon assembly located proximally on said cervical access catheter with an inflation lumen connecting said intrauterine balloon in fluid communication with said pilot balloon, and said method further comprises the steps of:

connecting an inflation syringe to said check valve for inflation of said intrauterine balloon; and observing inflation of said pilot balloon for a visual indication of inflation of said intrauterine balloon.

13. An apparatus for establishing access to the uterus and fallopian tube of a female which comprises:

an elongated cervical access catheter for establishing a working channel through the cervix into the uterus, wherein said working channel extends through said cervical access catheter, said cervical access catheter having a distal end with a distal end portion adjacent thereto and having a proximal end with a proximal end portion adjacent thereto, said cervical access catheter being anchorable in the cervical canal for establishing fluid tight extracorporeal access into the uterus through said working channel;

an inflatable intrauterine balloon located on said distal end portion of said cervical access catheter for passage through the cervical canal and inflation in the uterus;

a cervical retention disk slidably mounted on said cervical access catheter;

a fixation member attached to said cervical retention disk, said fixation member being slidably mounted on said cervical access catheter to position said disk against the anterior lip of the cervix while said inflatable balloon is in the uterus;

a locking mechanism mounted on said fixation member to selectively grip said cervical access catheter for holding said fixation member in place on said cervical access catheter;

an ostial access catheter for establishing access into the ostium of a fallopian tube, said ostial access catheter being selectively insertable through said working channel of said cervical access catheter to extend said distal end portion of said ostial access catheter beyond said distal end of said cervical access catheter, said ostial access catheter formed with a lumen and having a distal end with a distal end portion adjacent said distal end, and having a proximal end with a proximal end portion adjacent said proximal end, said ostial access catheter being guidable to position said distal end thereof into the ostium of the fallopian tube;

a fluid seal mounted in said working channel in said proximal portion of said cervical access catheter to establish a fluid barrier between said cervical access catheter and said ostial access catheter;

fallopian access means for establishing access into the fallopian tube, said fallopian access means being selectively insertable through said lumen of said ostial access catheter for advancement of said fallopian access means into the fallopian tube; and an O-ring mounted in said lumen in said distal portion of said ostial access catheter to establish a fluid seal between said ostial access catheter and said fallopian access means.

14. An apparatus as recited in claim 13 wherein said fallopian access means is a fallopian access catheter formed with a lumen having a distal end and a proximal end, said fallopian access catheter being insertable through said lumen of said ostial access catheter to extend said distal end of said fallopian access catheter beyond said distal end of said ostial access catheter, through the ostium of the fallopian tube and into the fallopian tube.

15. An apparatus as recited in claim 14 further comprising a fluid source selectively engageable with said working channel of said cervical assess catheter for injecting fluids into the uterus.

16. An apparatus as recited in claim 14 further comprising a fluid source selectively engageable with said lumen of said ostial access catheter for injecting fluids into the fallopian tube.

17. An apparatus as recited in claim 14 further comprising a fluid source selectively engageable with said lumen of said fallopian access catheter for injecting fluids into the fallopian tube.

18. An apparatus as recited in claim 14 further comprising a fluid access line attached to said cervical access catheter to establish fluid communication with said working channel, said fluid access line being joined in fluid communication with said working channel distally from said fluid seal.

19. An apparatus for establishing fluid communication with the uterus and fallopian tube of a female which comprises:

an elongated cervical access catheter for accessing the cervix, said cervical access catheter being anchorable in the cervical canal for establishing extracorporeal access into the uterus, said cervical access catheter being formed with a working channel having a distal end with a distal portion adjacent thereto and having a proximal end with a proximal end portion adjacent thereto, said working channel extending through said cervical access catheter;

an inflatable intrauterine balloon located on said distal end portion of said cervical access catheter for passage through the cervical canal and inflation in the uterus;

a cervical disk slidably mounted on said cervical access catheter;

a fixation member formed with said cervical disk, said fixation member being slidably mounted on said cervical access catheter to position said disk against the anterior lip of the cervix while said inflatable balloon is in the uterus;

a locking mechanism mounted on said fixation member having manipulable locking mechanism to selectively grip said cervical access catheter for holding said fixation member in place on said cervical access catheter;

a first fluid source selectively engageable in fluid communication with said working channel;

an ostial access catheter for establishing access to the ostium of a fallopian tube, formed with a lumen, said ostial access catheter having a distal end and a distal end portion adjacent said distal end thereof and a proximal end and a proximal end portion adjacent said proximal end thereof, said ostial access catheter being insertable through said first sealing means into said working channel of said cervical access catheter to extend said distal end portion of said ostial access catheter beyond said distal portion of said cervical access catheter, said distal end portion of said ostial access catheter being preformed for guidable placement of said distal end of said ostial access catheter against the ostium of the fallopian tube;

a second fluid source selectively engageable in fluid communication with said lumen of said ostial access catheter;

a fallopian access catheter for establishing access to the fallopian tubes, formed with a lumen, having a distal end and a proximal end, said fallopian access catheter being insertable through said second sealing means into said lumen of said ostial access catheter to extend said distal end of said fallopian access catheter beyond said distal end of said ostial access catheter, through the ostium of the fallopian tube and into the fallopian tube;

a third fluid source selectively engageable in fluid communication with said lumen of said fallopian access catheter;

an inflation lumen having a distal end and a proximal end, said distal end of said inflation lumen being connected with said inflatable intrauterine balloon for fluid communication therebetween;

a pilot balloon assembly connected in fluid communication with said proximal end of said inflation lumen;

a check valve connected in fluid communication with said pilot balloon assembly;

an inflation syringe engageable with said check valve for simultaneously inflating said intrauterine balloon and said pilot balloon;

a fluid sealing means mounted in said working channel in said proximal portion of said cervical access catheter to establish a fluid seal between said cervical access catheter and said ostial access catheter; and an O-ring mounted in said lumen in said proximal portion of said ostial access catheter to establish a fluid seal between said ostial access catheter and said fallopian access catheter.

\* \* \* \* \*